(12) United States Patent
Yang et al.

(10) Patent No.: US 10,517,492 B2
(45) Date of Patent: Dec. 31, 2019

(54) BIOSENSOR DEVICE AND PHYSIOLOGICAL MONITOR

(71) Applicant: Shenzhen Mindray Bio-Medical Electronics Co., Ltd., Shenzhen (CN)

(72) Inventors: Song Yang, Shenzhen (CN); Kun Jiao, Shenzhen (CN); Xianliang He, Shenzhen (CN); Peng Zhang, Shenzhen (CN); Xingliang Jin, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 0 days.

(21) Appl. No.: 16/523,740

(22) Filed: Jul. 26, 2019

(65) Prior Publication Data

US 2019/0343411 A1 Nov. 14, 2019

Related U.S. Application Data

(63) Continuation of application No. 16/038,624, filed on Jul. 18, 2018, which is a continuation of application No. PCT/CN2016/071586, filed on Jan. 21, 2016.

(51) Int. Cl.

| | |
|---|---|
| *A61B 5/04* | (2006.01) |
| *A61B 5/00* | (2006.01) |
| *A61B 5/1455* | (2006.01) |
| *A61B 5/0478* | (2006.01) |
| *A61B 5/021* | (2006.01) |
| *A61B 5/0205* | (2006.01) |
| *A61B 5/024* | (2006.01) |

(52) U.S. Cl.
CPC .................. *A61B 5/04* (2013.01); *A61B 5/00* (2013.01); *A61B 5/0205* (2013.01); *A61B 5/02141* (2013.01); *A61B 5/0478* (2013.01); *A61B 5/1455* (2013.01); *A61B 5/4821* (2013.01); *A61B 5/02427* (2013.01); *A61B 5/02438* (2013.01)

(58) Field of Classification Search
CPC ........... A61B 5/04; A61B 5/00; A61B 5/0205; A61B 5/02141; A61B 5/0478; A61B 5/1455; A61B 5/4821
USPC ......................................................... 340/573
See application file for complete search history.

(56) References Cited

U.S. PATENT DOCUMENTS

| | | | | |
|---|---|---|---|---|
| 4,719,909 A | * | 1/1988 | Micchia | A45D 44/00 128/858 |
| 2003/0225323 A1 | * | 12/2003 | Kiani | A61B 5/0478 600/323 |

(Continued)

FOREIGN PATENT DOCUMENTS

WO WO2015054312 * 4/2015

*Primary Examiner* — Omar Casillashernandez
(74) *Attorney, Agent, or Firm* — Kory D. Christensen

(57) ABSTRACT

A biosensor includes: a flexible base, a first sensor includes a first sensor main body; and a second sensor includes a second sensor main body that is detachably installed on the side face of the flexible base installed with the first sensor main body, and is arranged at intervals on the first sensor main body. The second sensor is detachably installed on the flexible base installed with the first sensor, and does not overlap with the first sensor, thereby allowing the second sensor to work together with the first sensor, thereby obtaining different physiological parameters. The second sensor can also be detached from the flexible base and used independently to increase user convenience.

30 Claims, 7 Drawing Sheets

(56) References Cited

U.S. PATENT DOCUMENTS

| | | | |
|---|---|---|---|
| 2005/0075553 A1* | 4/2005 | Sakai | A61B 5/02438 600/372 |
| 2006/0122474 A1* | 6/2006 | Teller | A61B 5/02055 600/300 |
| 2007/0225585 A1* | 9/2007 | Washbon | A61B 5/0478 600/393 |
| 2008/0287767 A1* | 11/2008 | Pasveer | A61B 5/0408 600/372 |
| 2014/0100432 A1* | 4/2014 | Golda | A61B 5/04325 600/301 |
| 2017/0105646 A1* | 4/2017 | Bryenton | A61B 5/6828 |
| 2017/0215811 A1* | 8/2017 | Newberry | A61B 5/7278 |
| 2018/0093121 A1* | 4/2018 | Matsuura | G09B 23/28 |
| 2018/0289328 A1* | 10/2018 | Hasegawa | A61B 5/6831 |
| 2018/0368710 A1* | 12/2018 | Yang | A61B 5/0205 |

\* cited by examiner

BIOSENSOR DEVICE AND PHYSIOLOGICAL MONITOR

CROSS-REFERENCE TO RELATED APPLICATIONS

This application is a continuation U.S. patent application Ser. No. 16/038,624, filed Jul. 18, 2018, for "Biosensor Device and Physiological Monitor," which is a continuation of PCT App. No. PCT/CN2016/071586, filed Jan. 21, 2016, for "Biosensor Device and Physiological Monitor Comprising the Biosensor Device," both of which are incorporated herein by reference.

TECHNICAL FIELD

The present disclosure relates to the field of medical instruments and, in particular, to a biosensor device and a physiological monitor including the biosensor device.

BACKGROUND

In the medical field, accurately determining physiological parameters of patients has important significance for doctors in the diagnosis and treatment of disease. At present, there are a large number of devices to monitor the physiological parameters of patients, providing doctors with a reference for diagnosis and treatment.

For example, during a surgical procedure for a patient, a certain amount of sedative is often used to keep the patient in general anesthesia, thereby reducing the patient's pain. Monitoring the anesthetic depth of the patient is very important to reducing the probability of physical trauma during and after the surgery. At present, electroencephalogram signals are often used to monitor the anesthetic depth of a patient. However, single electroencephalogram signals cannot completely reflect the patient's anesthesia due to the influence of various factors, such as certain drugs, cardiac arrest, cerebral ischemia, and cerebral hypoperfusion.

During surgery, a cerebral tissue blood oxygenation sensor is often used to obtain the local cerebral oxygen saturation of the patient by means of infrared spectrum analysis, so as to reduce the occurrence of cerebral complications in the surgery with anesthesia. However, with this method, the following situations often occur during the surgical procedure: (1) in the state of general anesthesia of a patient, it is determined, by measuring the cerebral tissue blood oxygenation, that anesthetic depth measurement is not affected by cerebral ischemia or cerebral hypoperfusion, such that the accuracy of the anesthetic depth measurement is improved; and (2) during some surgical procedures, it is not only necessary to adjust the setting of working parameters of an extracorporeal circulation machine by using a local cerebral tissue blood oxygenation measurement result, but also necessary to detect the anesthesia of the patient by using the electroencephalogram signals.

Therefore, in the above-mentioned surgery, a large number of biosensor devices (such as a tissue blood oxygen sensor and an anesthetic depth sensor) are often placed at the head of the patient. However, since each kind of sensor has its own separate cable and base material, the positions thereof often conflict, overlap, and interfere with each other, such that convenience is reduced and the conditions of patients cannot be precisely detected, resulting in an adverse effect for diagnosis and treatment.

SUMMARY

Disclosed herein is a biosensor device in which sensor positions will not overlap and mutual interference is avoided. Also disclosed herein is a physiological monitor capable of accurately reflecting physiological parameters.

In one aspect, a biosensor device includes: a flexible base have a first side and a second side that are opposite to each other; a first sensor having a first sensor body that is mounted at the first side of the flexible base; and a second sensor having a second sensor body that is detachably mounted at the first side of the flexible base at which the first sensor body is provided, and is spaced apart from the first sensor body.

With regard to the above-mentioned biosensor device, the second sensor is detachably mounted on the flexible base provided with the first sensor, and therefore, the second sensor can not only be used with the first sensor to measure different physiological parameters of the same patient, but also be used alone after being detached from the flexible base, thereby increasing the flexibility of use of the biosensor device. Moreover, since the second sensor does not overlap the first sensor, the first sensor and the second sensor do not interfere with each other while working together. As such, convenience and flexibility of user operations are enhanced, such that the first sensor and/or the second sensor may be selected as desired to detect different physiological states, and the mounting positions of the first sensor and the second sensor would not interfere with each other, thus avoiding an impact on the accuracy of monitoring.

In one embodiment, the first sensor is a tissue blood oxygen sensor, and the second sensor is an anesthetic depth sensor. In one embodiment, the second sensor body includes at least one electrode detachably mounted on the flexible base, the electrode protruding above a surface of a region of the flexible base that is not provided with the electrode.

In one embodiment, a snap female end is arranged at the first side of the flexible base, and the electrode is provided with a snap male end that is mateable with the snap female end, such that the electrode is detachably mounted on the flexible base.

In one embodiment, a side face of the flexible base is provided with a mounting counter-bore, the snap female end is arranged in the mounting counter-bore, and the electrode includes an electrode base, a foam arranged at one side of the electrode base and a conductive adhesive located on the foam, wherein the electrode base and the conductive adhesive are respectively located at two opposite sides of the foam, the electrode base matches the mounting counter-bore, the snap male end is arranged at one side of the electrode base that is not provided with the foam, and the flexible base located around the foam protrudes.

In one embodiment, the flexibility of the electrode base is more flexible than the flexible base, and the thickness of the electrode base is thicker than the flexible base.

In one embodiment, the first sensor body includes a light-emitting tube and a photosensitive tube, the light-emitting tube and the photosensitive tube being arranged apart at the first side of the flexible base.

In one embodiment, the first side of the flexible base is provided with mounting grooves, the shapes of the mounting grooves matching the shapes of the light-emitting tube and the photosensitive tube, and the light-emitting tube and the photosensitive tube being respectively accommodated in the mounting grooves.

In one embodiment, the flexible base located around the light-emitting tube and the photosensitive tube protrudes.

In one embodiment, the first side of the flexible base at which the first sensor body and the second sensor body are provided has a darker color.

In one embodiment, the flexible base is further provided with a through hole located between the first sensor body and the second sensor body.

In one embodiment, the second side of the flexible base is attached with a shielding layer.

In one embodiment, the biosensor device further includes a circuit board and a connector, the first sensor body and the second sensor body being both connected to the circuit board, and the circuit board being further connected to the connector.

In one embodiment, the circuit board includes a first circuit board with one end connected to the first sensor body and a second circuit board connected to the second sensor body, wherein the first circuit board is provided with a first conductor connection region, and the second circuit board is provided with a second conductor connection region, with the second conductor connection region matching the first conductor connection region and overlapping and contacting each other, and the first circuit board and the second circuit board being conducted through direct contact between the first conductor connection region and the second conductor connection region.

In one embodiment, the biosensor device further includes a connection structure, the first conductor connection region and the second conductor connection region overlapping and being fixed by the connection structure, and the connection structure wrapping around the first conductor connection region and the second conductor connection region, such that the two conductor connection regions are closely attached together.

In one embodiment, the biosensor device further includes a connection structure, the connection structure being integrally provided with the first conductor connection region of the first sensor, and the connection structure integrally provided with the first conductor connection region being in direct connection and conduction with the second conductor connection region.

In one embodiment, the first sensor and/or the second sensor further includes a flexible connection band, the flexible connection band connecting the first conductor connection region and the first sensor body and/or connecting the second conductor connection region and the second sensor body.

In one embodiment, the first sensor and the second sensor are arranged along a length direction of the flexible base and the circuit board protrudes from one end of the flexible base in the length direction, or the first sensor body and the second sensor body are symmetrically respectively arranged taking a central axis of the flexible base as a symmetric axis, and the circuit board overlaps the central axis of the flexible base and protrudes from one end at a middle portion of the flexible base.

In one embodiment, the biosensor device further includes a third sensor, with the third sensor having a third sensor body and a third conductor connection region that is detachably connected to the first conductor connection region.

In one embodiment, the biosensor device is provided with a connector and a cable socket detachably connected to the connector, and the first sensor body and the second sensor body may be simultaneously bonded and connected to the connector and are connected to the cable socket via the connector.

In another aspect, a biosensor device includes: a flexible base have a first side and a second side that are opposite to each other; a first sensor having a first sensor body and a first circuit board connected to the first sensor body that is mounted at the first side of the flexible base, and the first circuit board is provided with a first conductor connection region; a second sensor having a second sensor body and a second circuit board connected to the second sensor body, wherein the second sensor body is detachably mounted at the first side of the flexible base at which the first sensor body is provided and is spaced apart from the first sensor body, and the second circuit board is provided with a second conductor connection region; and a connection structure for connecting and conducting the first conductor connection region and the second conductor connection region, The first sensor is a tissue blood oxygen sensor, and the second sensor is an anesthetic depth sensor.

In one embodiment, the first conductor connection region and the second conductor connection region overlap, and the connection structure wraps around the first conductor connection region and the second conductor connection region.

In one embodiment, the connection structure presses against the first conductor connection region and the second conductor connection region, such that the first conductor connection region is in direct connection and conduction with the second conductor connection region; or the connection structure is separately in conduction and connection with the first conductor connection region and the second conductor connection region.

In one embodiment, the connection structure is integrally provided with the first conductor connection region of the first sensor, and the connection structure is in direct connection and conduction with the second conductor connection region.

In one embodiment, the biosensor device further includes a circuit board and a connector, with the circuit board having the first circuit board and the second circuit board, and the circuit board being further connected to the connector.

In one embodiment, the second conductor connection region of the second sensor is covered with a detachable insulation protection film.

In yet another aspect, a physiological monitor includes the above-mentioned biosensor device, and the physiological monitor further includes a signal processing device and a monitor, wherein the signal processing device is connected between the biosensor device and the monitor or is integrated into the monitor.

DETAILED DESCRIPTION

The present disclosure will be described below in a more comprehensive manner with reference to the relevant drawings. However, those skilled in the art will recognize that the present disclosure may be implemented in many different forms, and is not limited to the embodiments described herein.

Figure 1:
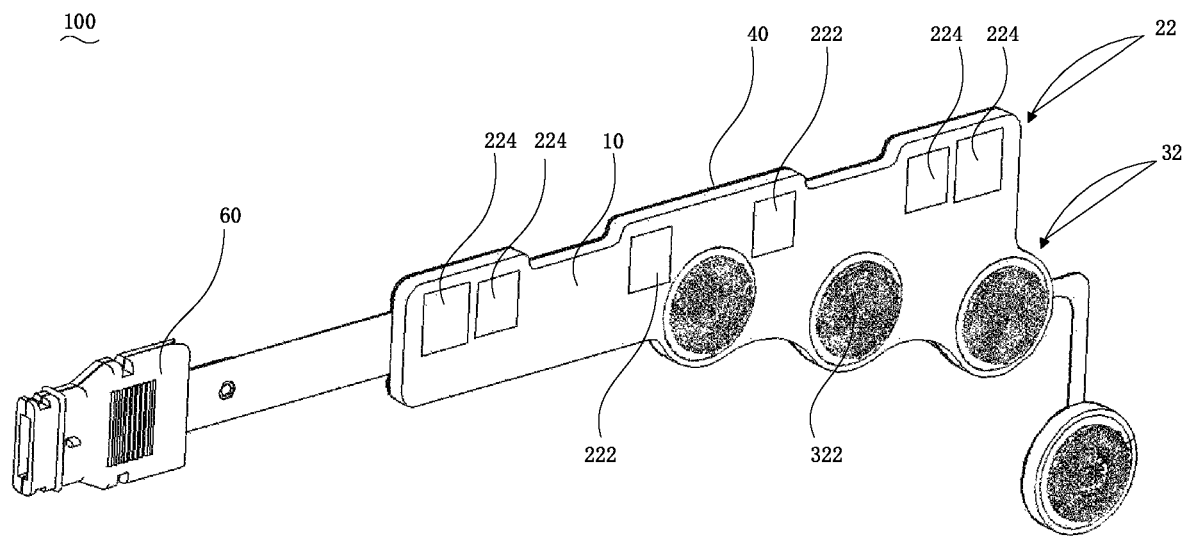
FIG. 1 is a structural schematic diagram of a biosensor device.

As shown in FIG. 1, a biosensor device 100 according to one embodiment is used for detecting physiological parameters of a patient. The biosensor device 100 includes a flexible base 10, a first sensor (not labeled in the figures) and a second sensor (not labeled in the figures).

The flexible base 10 includes a first side and a second side that are opposite to each other, and the first sensor includes a first sensor body 22, wherein the first sensor body 22 is mounted at the first side of the flexible base 10. The second sensor includes a second sensor body 32, wherein the second sensor body 32 is detachably mounted at the first side of the flexible base 10 at which the first sensor body 22 is provided, and is spaced apart from the first sensor body 22.

With regard to the above-mentioned biosensor device 100, the second sensor is detachably mounted on the flexible base 10 provided with the first sensor, and therefore the second sensor can not only be used with the first sensor to measure different physiological parameters of the same patient, but also be used alone after being detached from the flexible base 10, thereby increasing the use flexibility of the biosensor device 100. Moreover, since the second sensor does not overlap the first sensor, the first sensor and the second sensor would not interfere with each other while working together. As such, convenience and flexibility of user operations are realized, such that the first sensor and/or the second sensor may be selected as desired to detect different physiological states, and the mounting positions of the first sensor and the second sensor do not interfere with each other, thus avoiding a negative impact on the accuracy of monitoring.

In this embodiment, the first sensor is a tissue blood oxygen sensor for obtaining the local cerebral oxygen saturation of a patient by using infrared spectrum analysis, so as to reduce the occurrence of cerebral complications in a surgery with anesthesia. The second sensor is an anesthetic depth sensor for monitoring the physical conditions of the patient under general anesthesia, so as to reduce the probability of psychological trauma to the patient during and after the surgery. It may be understood that the functions of the first sensor and the second sensor are not limited thereto and may be set as desired. For example, the sensors can also be body temperature measurement sensors.

The first sensor cooperates with the second sensor, and in the state of general anesthesia of the patient, it may be determined, by using a cerebral tissue blood oxygenation result measured by the first sensor, that an anesthetic depth result measured by the second sensor is not affected by cerebral ischemia or cerebral hypoperfusion, such that the accuracy and reliability of anesthetic depth measurement are improved. In addition, during some surgical procedures, the setting of working parameters of an extracorporeal circulation machine may be adjusted by using a local cerebral tissue blood oxygenation measurement result detected by the first sensor, and the anesthesia of the patient can also be detected by the second sensor. As such, the first sensor works in cooperation with the second sensor so as to comprehensively reflect the condition of the patient, without reducing the detection accuracy and reliability due to the factors such as drugs, cardiac arrest, cerebral ischemia and cerebral hypoperfusion.

Continuing with reference to FIG. 1, the flexible base 10 of the biosensor device 100 has a length greater than a width thereof, and has a shape adapted to that of the forehead of a human body so as to be adhered to the forehead of the human body. The flexible base 10 forms a pattern hint at the second side of the flexible base 10 with a silk screen symbol or a shape structure, in order for accurate mounting of the first sensor and the second sensor.

One side of the flexible base 10 provided with the first sensor body 22 and the second sensor body 32 is adhered to the forehead and has a darker color, for example black, so as to prevent external light rays from affecting the measurement accuracy of the first sensor.

The second sensor body 32 includes one or more electrodes 322 detachably mounted to the flexible base 10, wherein the electrode 322 can amplify a cerebral spontaneous biological potential on the scalp of the patient, so as to obtain spontaneous and rhythmic electrical activities of a cerebral cell population.

Figure 2:
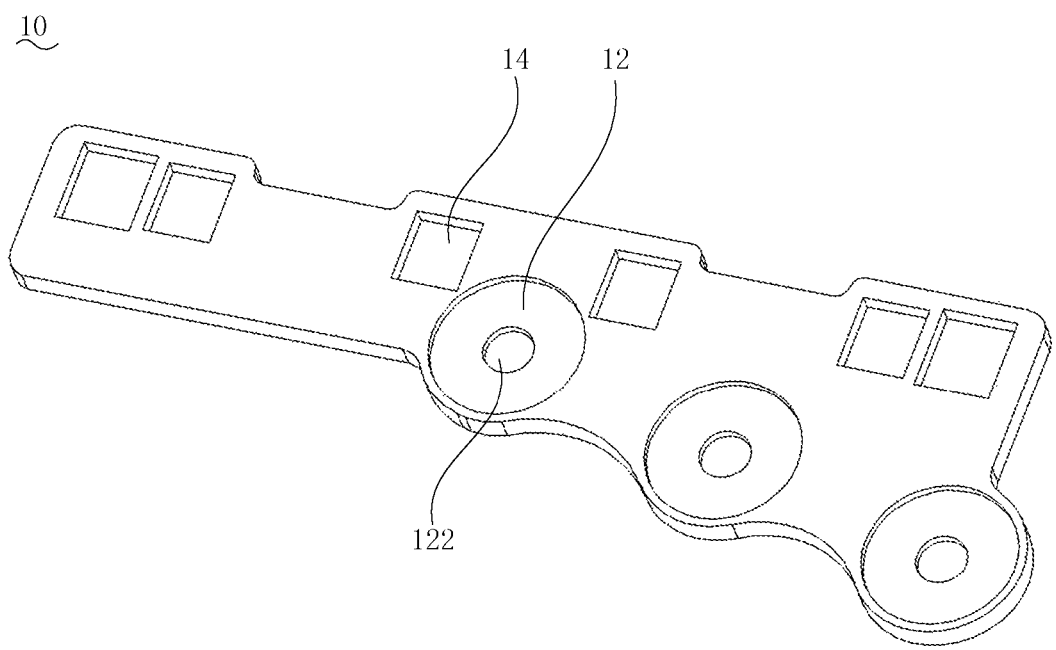
FIG. 2 is a structural schematic diagram of a flexible substrate of the biosensor device shown in FIG. 1.
Figure 3:
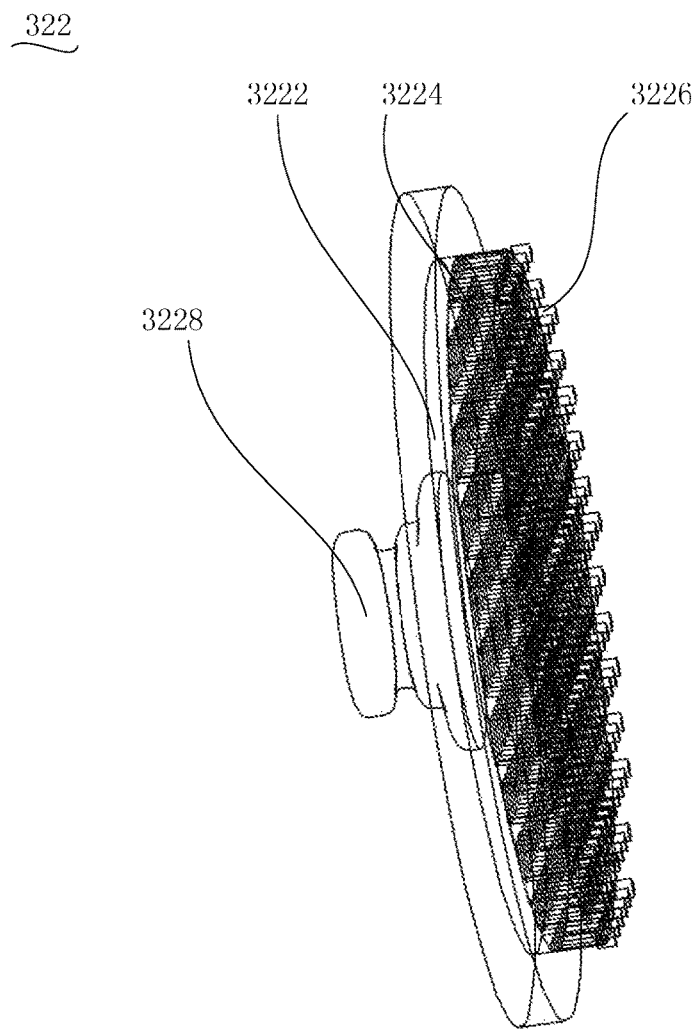
FIG. 3 is a structural schematic diagram of an electrode of the biosensor device shown in FIG. 1.
Figure 4:
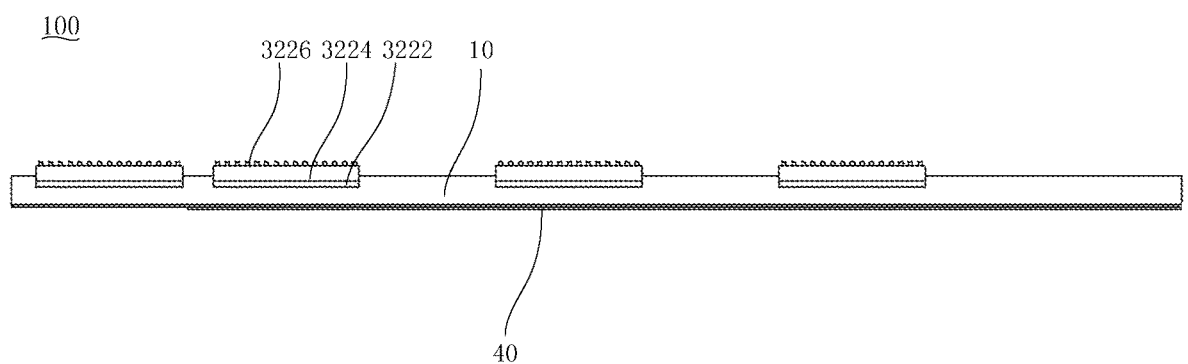
FIG. 4 is a schematic diagram of the mounting of the biosensor device shown in FIG. 1.

As shown in FIGS. 2, 3 and 4, the electrode 322 protrudes above a surface of a region of the flexible base 10 that is not provided with the electrode 322. An end surface of a part of the electrode 322 adhered to the patient keeps a certain distance from an end surface of a part of the flexible base 10 adhered to the patient, so as to ensure that the electrode 322 may be well adhered to the skin when the biosensor device 100 is attached onto the forehead of the human body, thereby avoiding the reduction in measurement precision due to the interference of photoelectric signals in the first sensor and the external environment. In this embodiment, there are a plurality of electrodes 322 to measure the potential at different sites on the forehead.

A snap female end 122 is arranged at the first side of the flexible base 10, and the electrode 322 is provided with a snap male end 3228 that is mateable with the snap female end 122, such that the electrode 322 is detachably mounted on the flexible base 10. During mounting, one may only need to press the snap male end 3228 into the snap female end 122, and during detaching, the electrode 322 may be pulled out with only a pulling force applied to the electrode 322. As such, the electrode 322 may be conveniently and quickly mounted on the flexible base 10 or detached from the flexible base 10 without causing a mechanical damage to the electrode 322.

Figure 11:
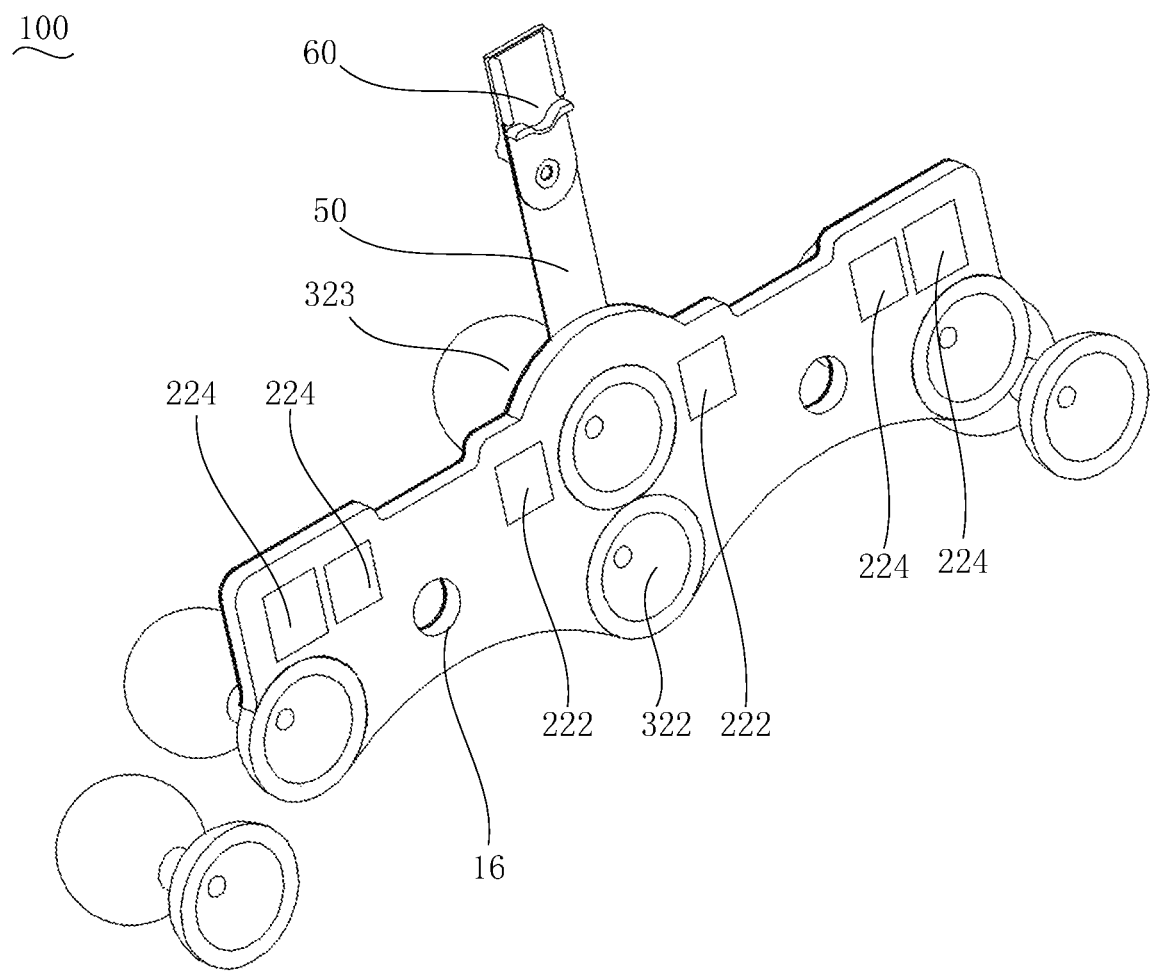
FIG. 11 is a structural schematic diagram of a biosensor device.

The first side of the flexible base 10 is provided with a mounting counter-bore 12, and the snap female end 122 is arranged in the mounting counter-bore 12. The electrode 322 is partially located within the mounting counter-bore 12 for secure mounting on the flexible base 10. It may be understood that the mounting manner of the electrode 322 is not limited thereto, and the electrode may be mounted by means of adsorption, etc. As shown in FIG. 11, in yet another embodiment, the second sensor body 32 further includes an adsorption member 323, wherein there is an attraction force between the electrode 322 and the adsorption member 323, and the adsorption member 323 is located at an opposite side to the electrode 322 so as to adsorb the electrode 322 onto the flexible base 10, such that the electrode 322 may be conveniently detached from the flexible base 10, and the electrode 322 is prevented from being damaged during the detaching process.

Specifically, the electrode 322 includes an electrode base 3222, a foam 3224 arranged at one side of the electrode base 3222, and a conductive adhesive 3226 located on the foam 3224, wherein the electrode base 3222 and the conductive adhesive 3226 are respectively located at two opposite sides of the foam 3224; the electrode base 3222 matches the mounting counter-bore 12 of the flexible base 10 in order to be accommodated in the mounting counter-bore 12; and the snap male end 3228 is arranged at one side of the electrode base 3222 not provided with the foam 3224, so as to cooperate with the snap female end 122. The conductive adhesive 3226 is directly in contact with the human body to directly obtain the biological potential. In this embodiment, the foam 3224 is a flexible foam, such that the electrode 322 may be well adhered to the skin of the patient.

Further, the flexibility of the electrode base 3222 is more flexible than the flexible base 10, and the thickness of the electrode base 3222 is thicker than the flexible base 10. Specifically, the electrode base 3222 is made of a soft and thin flexible material. This can on one hand avoid the case in which the patient feels uncomfortable due to the excessive adhesion of the electrode 322 to the forehead of the patient; and on the other hand avoid the problem that the electrode 322 cannot be well adhered to the skin of the patient due to the excessive stress of the flexible base 10 caused by the protrusion of the electrode above the flexible base 10, thereby preventing the working of the first sensor and the second sensor from being affected by the external environment. However, the flexible base 10 is made of a hard and thick flexible material. On one hand, this contributes to the fixing of the first sensor and the second sensor; and on the other hand, the flexible base 10 may be more closely adhered to a measured position of the forehead of the patient, leading to a larger adhesion force, thus preventing the measured position from being interfered by the external environment.

Figure 12:
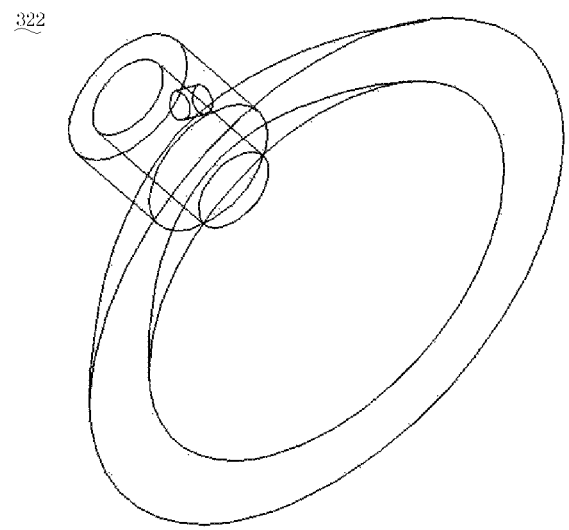
FIG. 12 is a structural schematic diagram of an electrode of the biosensor device shown in FIG. 11.
Figure 13:
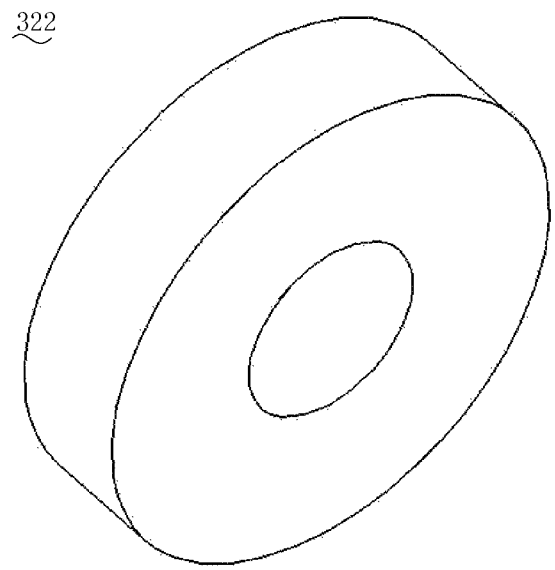
FIG. 13 is a structural schematic diagram of an electrode.

Referring to FIGS. 11, 12 and 13, in another embodiment, the electrode 322 has a plate shape or scoop shape, or is a cup-shaped self-filling conductive paste electrode 322. As shown in FIGS. 11 and 12, the plate-shaped electrode 322 recesses inwards from the edge toward the center. As shown in FIG. 13, the cup-shaped self-filling conductive paste electrode 322 is of a cylindrical structure with a filling hole arranged at the center and is used for filling conductive pastes, so as to measure the potential. It may be understood that the structure and type of the electrode 322 is not limited thereto, and the electrode may be of the other irregular shape, in order to be adapted to the position of the first sensor body 22 so as to avoid overlapping with each other. In other embodiments, the electrode 322 can also be a microneedle electrode to save a mounting space for the first sensor.

Referring to FIGS. 1 and 2 again, the first sensor body 22 includes a light-emitting tube 222 and a photosensitive tube 224, the light-emitting tube 222 and the photosensitive tube 224 being arranged apart at the first side of the flexible base 10. The first side of the flexible base 10 is provided with mounting grooves 14, with the shapes of the mounting grooves 14 matching the shapes of the light-emitting tube 222 and the photosensitive tube 224, and the light-emitting tube 222 and the photosensitive tube 224 being respectively accommodated in the mounting grooves 14. In this embodiment, the depths of the mounting grooves 14 are greater than the thicknesses of the light-emitting tube 222 and the photosensitive tube 224, such that the light-emitting tube 222 and the photosensitive tube 224 are completely accommodated in the mounting grooves 14.

In this embodiment, the first sensor body 22 includes two light-emitting tubes 222 and four photosensitive tubes 224, wherein the two dual-wavelength light-emitting tubes 222 emit light may having at least two wavelengths, and the light emitted from the light-emitting tubes 222 passes through the cerebral tissues of the patient and then is received by the photosensitive tubes 224 having different distances from the light-emitting tube 222, such that the blood oxygen content in the cerebral tissues is obtained by detecting the illumination intensity with the photosensitive tube 224.

Further, the first sensor bodies 22 are symmetrically arranged taking a central axis of the flexible base 10 as a symmetric axis. In this embodiment, the two light-emitting tubes 222 and the four photosensitive tubes 224 are symmetrically distributed taking a central perpendicular line of a connection line between the two light-emitting tubes 222 as a symmetric axis. Furthermore, the two light-emitting tubes 222 are adhered to an external side of superior sagittal sinus along the forehead, and the distance between the two light-emitting tubes 222 does not exceed the distance between the light-emitting tube 222 and the adjacent photosensitive tube 224. Specifically, in this embodiment, the distances between the light-emitting tube 222 and the two photosensitive tubes 224 on the same side as the light-emitting tube 222 are respectively 30 mm and 40 mm, and the distance between the two light-emitting tubes 222 is less than 30 mm, such that a better measurement effect is obtained.

In one embodiment, the flexible base 10 located around the electrode 322 protrudes and the flexible base 10 located around the light-emitting tube 222 and the photosensitive tube 224 protrude, such that a transition zone is formed between the first sensor body 22 and the second sensor body 32 to isolate the mutual influence between optical signals and electrical signals, so as to enable the flexible base 10 in the transition zone to be better adhered to the skin of the patient.

In one embodiment, the second side of the flexible base 10 is attached with a shielding layer 40, so as to reduce the impact of external photoelectric signals on the measurement precision.

Referring to FIG. 1 again, the biosensor device 100 further includes a circuit board (not labeled in the figures) for data transmission and a connector 60.

The circuit board is arranged at the second side of the flexible base 10, that is, the side of the flexible base 10 not provided with the first sensor and the second sensor; the first sensor body 22 and the second sensor body 32 are both connected to the circuit board; the other end of the circuit board not connected to the first sensor body 22 and the second sensor body 32 is connected to the connector 60; and the connector 60 is communicatively connected to a monitor. As such, the first sensor body 22 and the second sensor body 32 are communicatively connected to the monitor via the connector 60, such that a doctor obtains the physiological parameters of the patient. Since the first sensor and the second sensor use the same circuit board for transmission, the situation where inconvenience of surgery is caused to the doctor due to cable stacking is avoided. In this embodiment, the circuit board is a flexible circuit board, and thus has a better flexibility.

Figure 5:
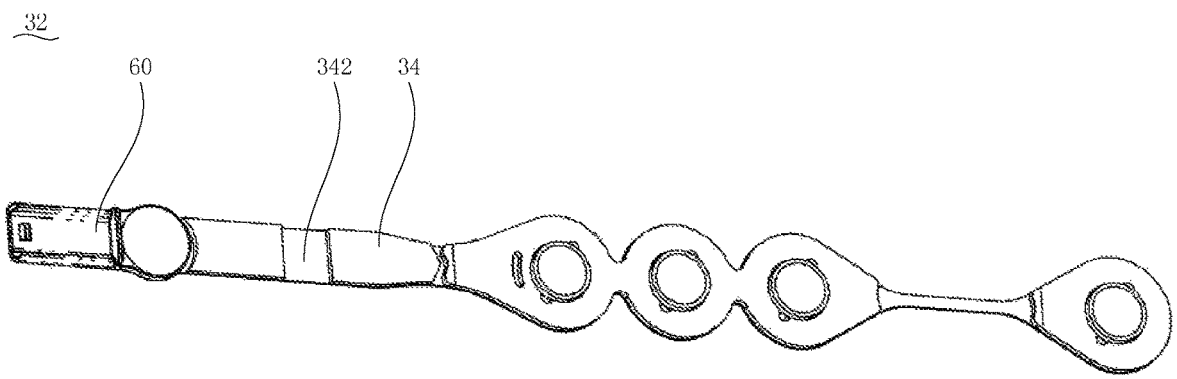
FIG. 5 is a schematic diagram of a second sensor of the biosensor device shown in FIG. 1.
Figure 6:
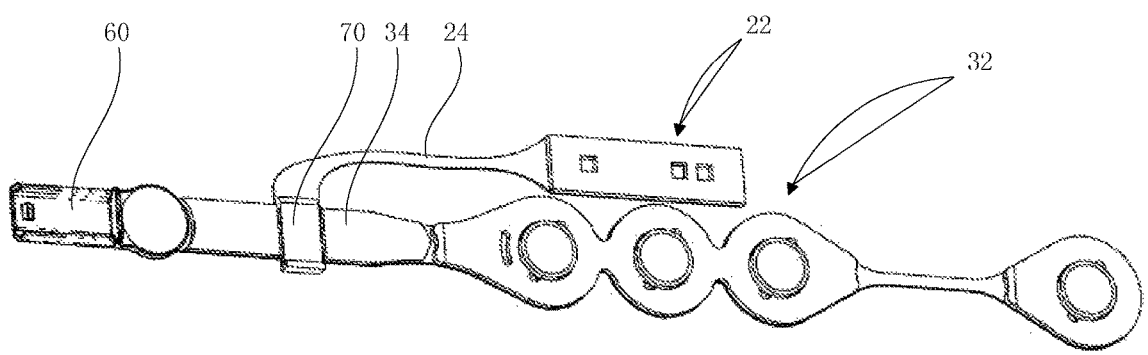
FIG. 6 is a schematic diagram of the connection of a first sensor and a second sensor of the biosensor device shown in FIG. 1.

Referring to FIGS. 5 and 6, the circuit board includes a first circuit board with one end connected to the first sensor body 22 and a second circuit board 34 connected to the second sensor body 32. The first circuit board is provided with a first conductor connection region (not labeled in the figures), and the second circuit board is provided with a second conductor connection region 342, with the second conductor connection region 342 matching the first conductor connection region and overlapping and contacting each other, and the first circuit board and the second circuit board 34 being conducted through direct contact between the first conductor connection region and the second conductor connection region. Specifically, conductors of the first conductor connection region and the second conductor connection region 342 are exposed so that the first conductor connection region and the second conductor connection region 342 may be communicated through direct contact, and thus both of the first sensor and the second sensor transmit data by using the circuit board.

The biosensor device 100 further includes a connection structure for connecting and conducting the first conductor connection region and the second conductor connection region. In this embodiment, the first conductor connection region and the second conductor connection region 342 overlap and are fixed by the connection structure 70, and the connection structure 70 wraps around the first conductor connection region and the second conductor connection region 342, such that the first conductor connection region and the second conductor connection region 342 are closely attached together through a pressure force so as to achieve a conductive connection. Specifically, in this embodiment, the connection structure 70 is a connection clamp for clamping the first conductor connection region and the second conductor connection region 342.

It may be understood that the structure of the connection structure 70 is not limited thereto, and in other embodiments, the connection structure 70 may be of an elastic sheet shape, thimble shape, tip-bead shape structure, etc. In other embodiments, the connection structure 70 can also be integrally provided with the first conductor connection region of the first sensor, and the connection structure 70 integrally provided with the first conductor connection region is directly connected to the second conductor connection region 342 so as to achieve the conduction with the second conductor connection region 342. In another embodiment, the connection structure 70 can also be separately in conduction and connection with the first conductor connection region and the second conductor connection region 342.

Further, the first sensor and the second sensor are provided with one of a positioning hole or a positioning shaft, and the other one of the positioning hole or the positioning shaft is arranged on the connection structure 70, wherein the positioning hole cooperates with the positioning shaft so as to facilitate the positioning of the connection clamp and ensure the degree of alignment between the first conductor connection region and the second conductor connection region 342.

Figure 7:
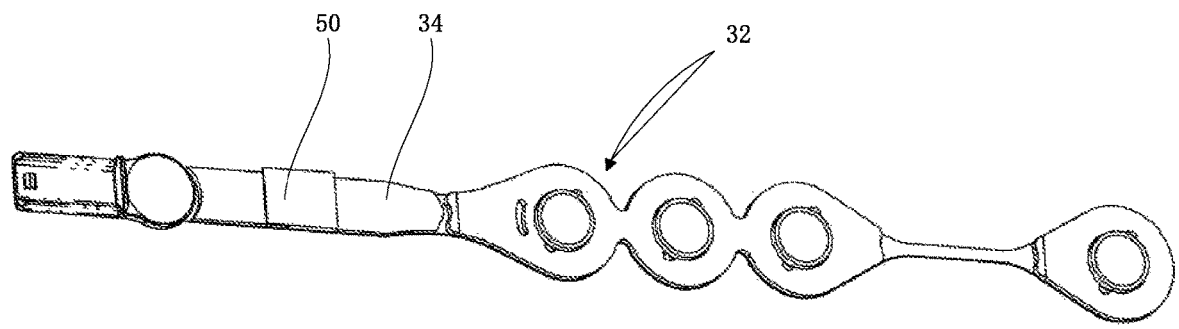
FIG. 7 is a schematic diagram of the second sensor, provided with an insulation thin film, of the biosensor shown in FIG. 5.

As shown in FIG. 7, the second conductor connection region 342 of the second sensor is further covered with a detachable insulation protection film 50. When the second sensor is used alone, the second conductor connection region 342 may be prevented from interfering with the measurement due to the conductor exposure thereof, and the safety of the patient is protected.

Further, the first sensor and/or the second sensor further comprise(s) a flexible connection band 24. By taking the first sensor as an example, the flexible connection band 24 connects the first conductor connection region and the first sensor body 22, such that the parameters monitored by the first sensor body 22 are transferred to the first conductor connection region through the flexible connection band 24. Furthermore, the shape and length of the flexible connection band 24 are adapted to the measured position of the first sensor body 22, so as to reduce the interference of a bending stress.

As such, the first sensor and the second sensor can share one circuit board, and the two sensors can also be respectively and separately used, such that the two sensors are prevented from being wasted because of simultaneous scrappage thereof due to the difference in service life and the stress interference between the two sensors can also be prevented, and meanwhile, it is ensured that the second sensor has no any other structure cumbersome and burdensome when used alone.

In other embodiments, the first sensor body 22 and the second sensor body 32 may be simultaneously bonded and connected to the connector 60 and are connected to a cable socket via the connector 60, so as to achieve cable sharing.

Figure 10:
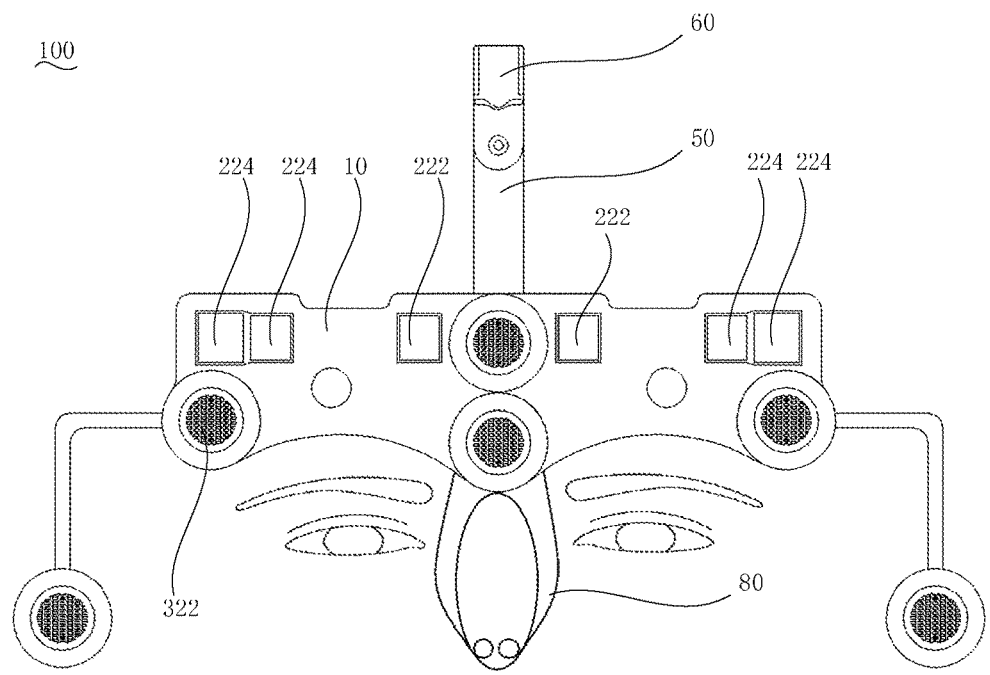
FIG. 10 is a schematic diagram of the use of the biosensor device shown in FIG. 9.

As shown in FIG. 10, the biosensor device 100 further includes a third sensor 80, the third sensor 80 being a nose clip-type pulse blood oxygen sensor for measuring the pulse and blood oxygen content of the nose. The third sensor 80 includes a third conductor connection region to connect to the first conductor connection region of the first sensor. As such, while more physiological parameters of the patient are obtained, the case where the inconvenience is caused to the doctor's surgical operation due to the stacking of a plurality of sensors located at the head is avoided.

Referring to FIG. 1 again, in this embodiment, the first sensor and the second sensor are arranged along the length direction of the flexible base 10, and the flexible circuit board protrudes from one end of the flexible base 10 in the length direction so as to be adhered to one side of the forehead of the patient.

Specifically, in the embodiment shown in FIG. 1, the circuit board is arranged at one end of the flexible base 10, and the circuit board, the flexible base 10 and the connector 60 are substantially in the same straight line; the light-emitting tube 222 and the photosensitive tube 224 are substantially in the same straight line; and the biosensor device 100 includes four electrodes 222, wherein one electrode is located in the middle portion of the flexible base 10 along the length direction, and the other three electrodes 222 are all arranged at the same side, away from the connector 60, of the electrode 222 located in the middle portion. As such, the first sensor, the second sensor and the connector 60 will have no interference among one another and may be conveniently adhered to the forehead of the person, and the second sensor is only distributed at one side of the forehead.

Figure 8:
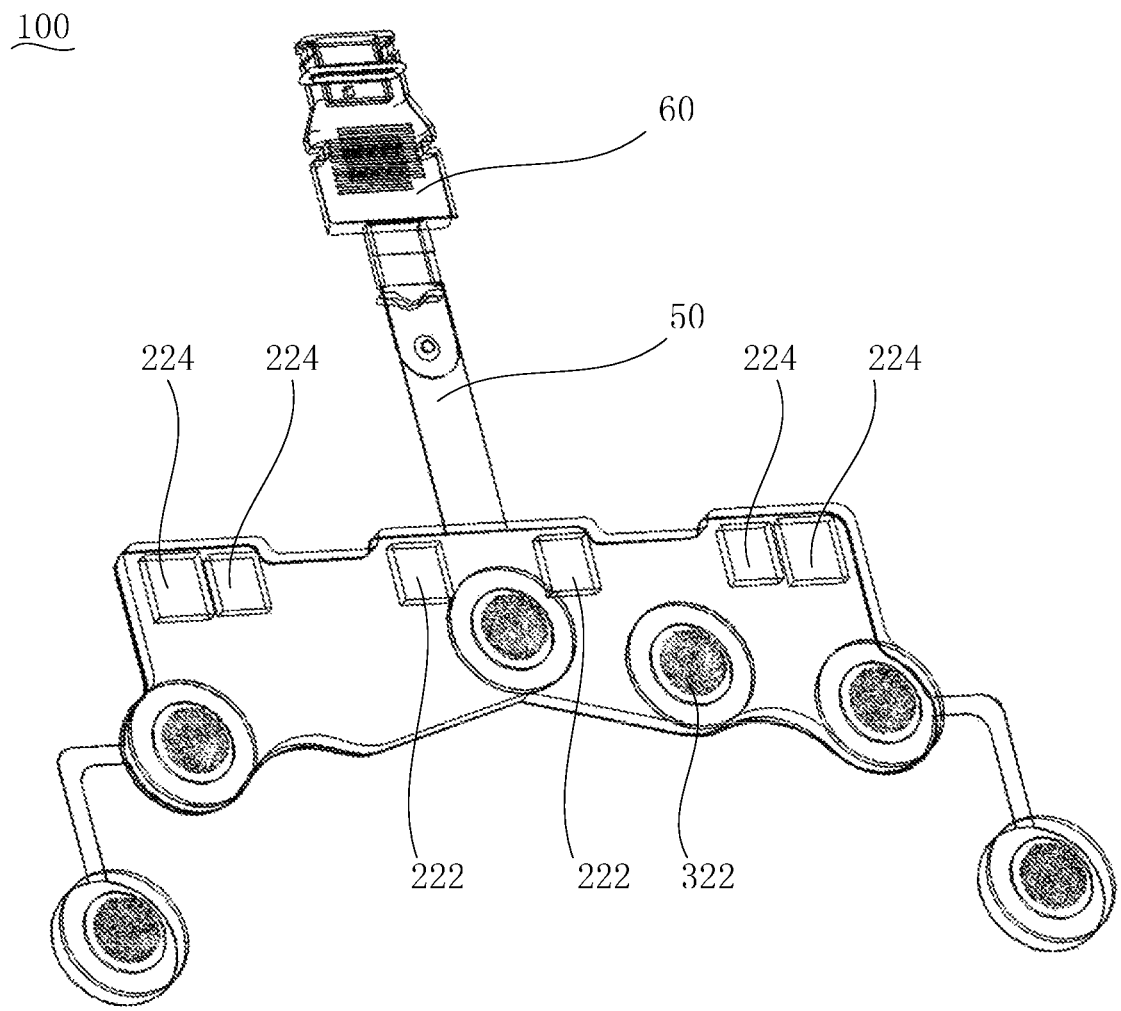
FIG. 8 is a structural schematic diagram of a biosensor device.
Figure 9:
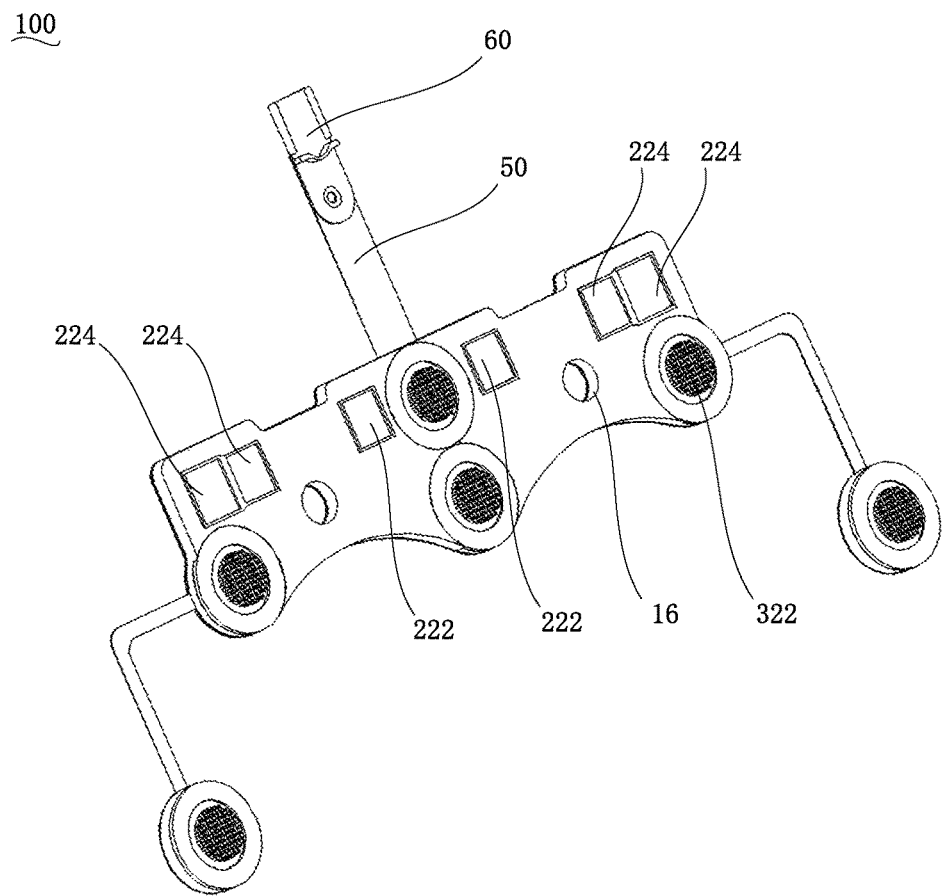
FIG. 9 is a structural schematic diagram of a biosensor device.

Referring to FIGS. 8, 9 and 10, in another embodiment, the contour of the biosensor device 100 approximates the contour of the forehead. The first sensor body 22 and the second sensor body 32 are respectively and symmetrically arranged taking a central axis of the flexible base 10 as a symmetric axis, and the flexible circuit board overlaps the central axis of the flexible base 10 and protrudes from one end at a middle portion of the flexible base 10, so as to be symmetrically adhered onto the forehead of the patient. In this embodiment, the third sensor 80 is located at the other end corresponding to the flexible circuit board, and is in an opposite direction to an extending direction of the flexible circuit board so as to be adhered to the nose of the patient.

Specifically, in the embodiments of FIGS. 8-10, the circuit board is arranged at a middle portion of one side of the flexible base 10, the connector 60 is connected to one end of the circuit board away from the flexible base 10, the first sensor is located between the connector 60 and the second sensor, and a plurality of electrodes 222 are distributed in the middle portion of the flexible base 10 and at two sides of the middle portions. As such, the first sensor, the second sensor and the connector 60 will have no interference among one another and may be conveniently adhered to the forehead of the person, and the second sensors are distributed at two sides of the forehead.

Further, the flexible base 10 is further provided with a through hole 16 located between the first sensor body 22 and the second sensor body 32 to increase the flexibility of the flexible base 10, thereby avoiding the situation where the effect of adhesion between the first sensor body 22 and the second sensor body 32 and the patient's forehead is influenced due to a larger region of adhesion of the flexible base 10 to the patient's forehead site. In this embodiment, the number of through holes 16 is two. It may be understood that the number and position of the through holes 16 are not limited and may be set as desired.

It may be understood that the settings of the shape of the flexible base and the position of the electrode 322 are not limited thereto, and they may be set as desired.

With regard to the above-mentioned biosensor device 100, the second sensor is detachably mounted on the flexible base 10 provided with the first sensor and is detachably connected to the first sensor, and the two sensors are commonly connected to the circuit board via the first conductor connection region and the second conductor connection region 342. As such, the first sensor and the second sensor can realize cable sharing, such that the user operations are simplified and the interference of multiple cables is reduced. Meanwhile, the second sensor may be detached from the flexible base 10, such that the first sensor and the second sensor may be separately used without interfering with each other, and may be replaced according to their respective service life, thus reducing costs.

Figure 14:
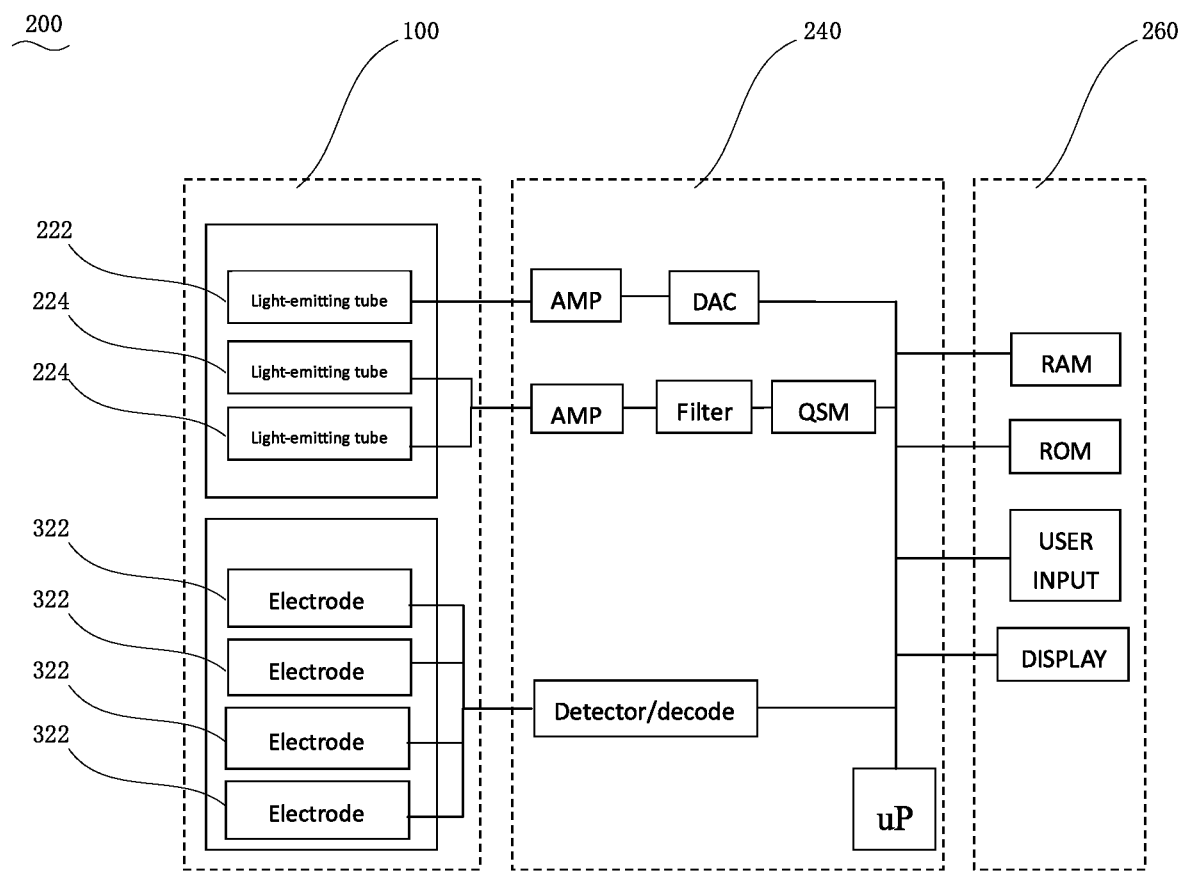
FIG. 14 is a schematic diagram of a physiological monitor.

As shown in FIG. 14, a physiological monitor 200 of this embodiment includes the above-mentioned biosensor device 100, and further includes a signal processing device 240 and a monitor 260, wherein the signal processing device 240 is connected between the biosensor device 100 and the monitor 260. In another embodiment, the signal processing device 240 can also be integrated into the monitor 260.

The above-mentioned physiological monitor 200 transmits the physiological parameter data obtained by the biosensor device 200 to the monitor 260 via the signal processing device 240 for display to the operator, such that the operator can intuitively observe the physiological parameters of the patient, thereby performing accurate diagnosis and treatment.

In this embodiment, specifically, the signal processing device 240 includes: an amplifier (AMP) and a digital-to-analog converter (DAC) which are connected to the light-emitting tube 222 of the first sensor; an amplifier (AMP), a filter and a quasi-static memory (OSM) which are connected to the photosensitive tube 224; and a detector (Detector/Decode) connected to the electrode 322. The data obtained by the biosensor device 100 are processed by the above-mentioned devices, and are sent to the monitor 260 for display.

The monitor 260 includes a random access memory (RAM), a read only memory (ROM), a user input unit (User Input) and a display unit (Display) for storing, reading, and displaying the physiological parameters sent by the signal processing device 240, and sending, by the user input unit, an instruction to the signal processing device 240.

The signal processing device 240 may be connected to the monitor 260 via a cable, and can also be wirelessly connected to the monitor 260, thereby simplifying the wiring structure of the physiological monitor 200 and making the structure of the entire device more compact.

The above-mentioned physiological monitor 200 can accurately monitor, by the biosensor device 100, the physiological parameters of the patient in real time, and transmit, by the signal processing device 240, the physiological data to the monitor 260 in real time, for supplying a quick and direct reaction to the operator, thus having a relatively high efficiency and accuracy.

The various technical aspects of the embodiments described above may be combined in any manner. For the sake of brevity of description, not all of the possible combinations of the various technical aspects in the above-mentioned embodiments are described. However, as long as there is no contradiction among the combinations of these technical aspects, all should be considered to be encompassed within the scope of the description.

The above-mentioned embodiments merely represent several implementations of the present disclosure, giving specifics and details thereof, but should not be understood as limiting the scope of the present patent of disclosure thereby. It should be noted that a person of ordinary skill in the art could also make some alterations and improvements without departing from the spirit of the present disclosure and these would all fall within the scope of protection of the present disclosure. Therefore, the scope of protection of the present patent of disclosure shall be in accordance with the appended claims.

What is claimed is:

1. A biosensor device, comprising:
   a flexible base comprising a first side and a second side that are opposite to each other;
   a first sensor comprising a first sensor body, wherein the first sensor body is mounted at the first side of the flexible base; and
   a second sensor comprising a second sensor body, wherein the second sensor body is detachably mounted at the first side of the flexible base at which the first sensor body is provided, and is spaced apart from the first sensor body, if the second sensor is mounted on the flexible base, the first and second sensors are capable of being used together to measure different physiological parameters of a same patient, and if the second sensor is detached from the flexible base, the first and second sensors are capable of being used separately to measure different physiological parameters of different patients.

2. The biosensor device of claim 1, wherein the first sensor is a tissue blood oxygen sensor, and the second sensor is an anesthetic depth sensor.

3. The biosensor device of claim 1, wherein the second sensor body comprises at least one electrode detachably mounted on the flexible base, the electrode protruding above a surface of a region of the flexible base that is not provided with the electrode.

4. The biosensor device of claim 3, wherein the second sensor body includes an adsorption member, and the adsorption member is located at an opposite side to the electrode so as to adsorb the electrode onto the flexible base.

5. The biosensor device of claim 1, wherein the first sensor body comprises a light-emitting tube and a photosensitive tube, the light-emitting tube and the photosensitive tube being arranged apart at the first side of the flexible base.

6. The biosensor device of claim 1, wherein the first side of the flexible base at which the first sensor body and the second sensor body are provided has a darker color.

7. The biosensor device of claim 1, wherein the flexible base is further provided with a through hole located between the first sensor body and the second sensor body.

8. The biosensor device of claim 1, wherein the second side of the flexible base is attached with a shielding layer.

9. The biosensor device of claim 1, further comprising a circuit board and a connector, the first sensor body and the second sensor body being both connected to the circuit board, and the circuit board being further connected to the connector.

10. A physiological monitor, comprising:
a biosensor device, comprising:
a flexible base comprising a first side and a second side that are opposite to each other;
a first sensor comprising a first sensor body, wherein the first sensor body is mounted at the first side of the flexible base; and
a second sensor comprising a second sensor body, wherein the second sensor body is detachably mounted at the first side of the flexible base at which the first sensor body is provided, and is spaced apart from the first sensor body, if the second sensor is mounted on the flexible base, the first and second sensors are capable of being used together to measure different physiological parameters of a same patient, and if the second sensor is detached from the flexible base, the first and second sensors are capable of being used separately to measure different physiological parameters of different patients;
a signal processing device; and
a monitor, wherein the signal processing device is connected between the biosensor device and the monitor or is integrated into the monitor.

11. The physiological monitor of claim 10, wherein the first sensor is a tissue blood oxygen sensor, and the second sensor is an anesthetic depth sensor.

12. The physiological monitor of claim 10, wherein the second sensor body comprises at least one electrode detachably mounted on the flexible base, the electrode protruding above a surface of a region of the flexible base that is not provided with the electrode.

13. The physiological monitor of claim 12, wherein a snap female end is arranged at the first side of the flexible base, and the electrode is provided with a snap male end that is mateable with the snap female end, such that the electrode is detachably mounted on the flexible base.

14. The physiological monitor of claim 13, wherein a side face of the flexible base is provided with a mounting counterbore, the snap female end is arranged in the mounting counterbore, and the electrode comprises an electrode base, a foam arranged at one side of the electrode base and a conductive adhesive located on the foam, wherein the electrode base and the conductive adhesive are respectively located at two opposite sides of the foam, the electrode base matches the mounting counterbore, the snap male end is arranged at one side of the electrode base that is not provided with the foam, and the flexible base located around the foam protrudes.

15. The physiological monitor of claim 14, wherein the electrode base is more flexible than the flexible base, and the electrode base is thicker than the flexible base.

16. The physiological monitor of claim 12, wherein the second sensor body includes an adsorption member, and the adsorption member is located at an opposite side to the electrode so as to adsorb the electrode onto the flexible base.

17. The physiological monitor of claim 10, wherein the first sensor body comprises a light-emitting tube and a photosensitive tube, the light-emitting tube and the photosensitive tube being arranged apart at the first side of the flexible base.

18. The physiological monitor of claim 17, wherein the first side of the flexible base is provided with mounting grooves, shapes of the mounting grooves matching shapes of the light-emitting tube and the photosensitive tube, and the light-emitting tube and the photosensitive tube being respectively accommodated in the mounting grooves.

19. The physiological monitor of claim 17, wherein the flexible base located around the light-emitting tube and the photosensitive tube protrudes.

20. The physiological monitor of claim 10, wherein the first side of the flexible base at which the first sensor body and the second sensor body are provided has a darker color.

21. The physiological monitor of claim 10, wherein the flexible base is further provided with a through hole located between the first sensor body and the second sensor body.

22. The physiological monitor of claim 10, wherein the second side of the flexible base is attached with a shielding layer.

23. The physiological monitor of claim 10, wherein the biosensor device comprises a circuit board and a connector, the first sensor body and the second sensor body being both connected to the circuit board, and the circuit board being further connected to the connector.

24. The physiological monitor of claim 23, wherein the circuit board comprises a first circuit board with one end connected to the first sensor body and a second circuit board connected to the second sensor body, wherein the first circuit board is provided with a first conductor connection region, and the second circuit board is provided with a second conductor connection region, with the second conductor connection region matching the first conductor connection region and overlapping and contacting with each other, and the first circuit board and the second circuit board being conducted through direct contact between the first conductor connection region and the second conductor connection region.

25. The physiological monitor of claim 24, wherein the biosensor device comprises a connection structure, the first conductor connection region and the second conductor connection region overlapping and being fixed by the connection structure, and the connection structure wrapping around the first conductor connection region and the second conductor connection region, such that the two conductor connection regions are closely attached together.

26. The physiological monitor of claim 24, wherein the biosensor device comprises a connection structure, the connection structure being integrally provided with the first conductor connection region of the first sensor, and the connection structure being in direct connection and conduction with the second conductor connection region.

27. The physiological monitor of claim 24, wherein the first sensor and/or the second sensor further comprise a flexible connection band, the flexible connection band connecting the first conductor connection region and the first sensor body and/or connecting the second conductor connection region and the second sensor body.

28. The physiological monitor of claim 24, wherein the first sensor and the second sensor are arranged along a length direction of the flexible base and the circuit board protrudes from one end of the flexible base in the length direction, or the first sensor body and the second sensor body are symmetrically respectively arranged with a central axis of the flexible base as a symmetric axis, and the circuit board overlaps the central axis of the flexible base and protrudes from one end at a middle portion of the flexible base.

29. The physiological monitor of claim 24, wherein the biosensor device comprises a third sensor, the third sensor comprising a third sensor body and a third conductor connection region, wherein the third conductor connection region is detachably connected to the first conductor connection region.

30. The physiological monitor of claim 10, wherein the biosensor device is provided with a connector and a cable socket detachably connected to the connector, and the first sensor body and the second sensor body are capable of being simultaneously bonded and connected to the connector and are connected to the cable socket via the connector.

\* \* \* \* \*